(12) United States Patent
Yellin et al.

(10) Patent No.: US 10,543,087 B2
(45) Date of Patent: Jan. 28, 2020

(54) DEVICE AND METHOD FOR DELIVERY OF AN IMPLANT THROUGH A CATHETER

(71) Applicant: VALCARE, INC., Newport Beach, CA (US)

(72) Inventors: Nadav Yellin, Ramat Gan (IL); Samuel M. Shaolian, Newport Beach, CA (US); Matan Gedulter, Givat Ella (IL); Boaz Schwarz, Tel Aviv (IL); Tsahi Grimberg, Kfar Saba (IL); Viktoria Protsenko, Bat Yam (IL); Daniel Rapoport, Kfar Menahem (IL)

(73) Assignee: VALCARE, INC., Newport Beach, CA (US)

( * ) Notice: Subject to any disclaimer, the term of this patent is extended or adjusted under 35 U.S.C. 154(b) by 219 days.

(21) Appl. No.: 15/730,080

(22) Filed: Oct. 11, 2017

(65) Prior Publication Data

US 2018/0098849 A1 Apr. 12, 2018

Related U.S. Application Data

(60) Provisional application No. 62/406,765, filed on Oct. 11, 2016.

(51) Int. Cl.
*A61F 2/24* (2006.01)
*A61B 17/34* (2006.01)
*A61F 2/95* (2013.01)

(52) U.S. Cl.
CPC ........ *A61F 2/2436* (2013.01); *A61B 17/3468* (2013.01); *A61F 2/2466* (2013.01); *A61F 2/95* (2013.01)

(58) Field of Classification Search
CPC .. A61B 17/3468; A61F 2/2427; A61F 2/2436; A61F 2/2466; A61F 2/95; A61F 2/954; A61F 2/962; A61F 2002/9534
See application file for complete search history.

(56) References Cited

U.S. PATENT DOCUMENTS

2003/0050649 A1 3/2003 Brock et al.
2008/0065011 A1 3/2008 Marchand et al.
(Continued)

FOREIGN PATENT DOCUMENTS

WO 2015052629 A1 4/2015
WO 2016040526 A1 3/2016

OTHER PUBLICATIONS

International Search Report and Written Opinion for PCT/US2017/56138 dated Jan. 8, 2018.
(Continued)

*Primary Examiner* — Melanie R Tyson
(74) *Attorney, Agent, or Firm* — Pepper Hamilton LLP

(57) ABSTRACT

Disclosed herein is a delivery system for percutaneous heart valve repair, the delivery system including a steerable sheath configured to provide percutaneous access into a heart and to deliver an implant. The system may also have a steering mechanism configured to manipulate and orient the implant, a ball joint mechanism configured to connect the steerable sheath to the steering mechanism, a main knob assembly configured to advance and retract a multilumen shaft assembly, a stabilizing tool including a plurality of prongs configured to engage the implant within the heart to make an intimate contact with the heart tissue using a stabilizer and a tongue assembly, and a back assembly including: the actuation mechanism, a suture routing mechanism, a tip lock mechanism, and a back cover configured to protect all sutures being cut by mistake.

20 Claims, 18 Drawing Sheets

(56) References Cited

U.S. PATENT DOCUMENTS

2010/0204713 A1  8/2010  Ruiz Morales
2010/0262232 A1  10/2010  Annest
2014/0364939 A1  12/2014  Deshmukh et al.
2015/0366666 A1  12/2015  Khairkhahan et al.

OTHER PUBLICATIONS

International Search Report and Written Opinion for PCT/US2017/044129 dated Sep. 27, 2017.

DEVICE AND METHOD FOR DELIVERY OF AN IMPLANT THROUGH A CATHETER

CROSS-REFERENCED TO RELATED APPLICATIONS

The present application claims benefit of priority under 35 U.S.C. 119(e) to the filing date of U.S. Provisional Patent Application 62/406,765 filed Oct. 11, 2016, entitled, "DEVICE AND METHOD FOR DELIVERY OF AN IMPLANT THROUGH A CATHETER," the contents of which is incorporated herein by reference in their entirety.

BACKGROUND

The present disclosure is generally related to a device and method for delivering an implant through a catheter.

Generally, percutaneous procedures relate to medical procedures by which internal organs or tissue are accessed via a small incision in the skin rather than a more invasive approach in which the internal organs or tissue are exposed. A percutaneous approach is typically used in vascular procedures (e.g., angioplasty and stenting). The term "percutaneous" specifically refers to the access modality of a medical procedure whereby a medical device is introduced into a patient's blood vessel via a needle or catheter.

Functional mitral and/or tricuspid regurgitation are the most common types of valve pathologies and are usually associated with mitral valve disease (MVD). Currently, the majority of patients with mitral and/or tricuspid regurgitation require surgical treatment, but a large portion of the population does not receive such treatment due to the high risk and complexity associated with invasive procedures (e.g., open heart surgery).

Minimally invasive percutaneous treatments are being developed to address this need. Such processes can be generally characterized as treating structural heart diseases through a catheter to reduce the incidence of open heart surgical intervention. This not only provides a safer and more efficient treatment, but also may provide the only viable treatment available, particularly for high risk patients.

SUMMARY

A delivery system and methods for minimally invasive percutaneous procedures for treatment of mitral and/or tricuspid regurgitation are disclosed. The delivery system includes a set of mechanisms configured to introduce the implant, actuate the implant functions, manipulate the implant within a target site, align the implant to the anatomy, create intimate contact between the implant and the anatomy, release the implant within the target site, and safely retrieve the delivery system.

The delivery system may include a steerable sheath configured to provide percutaneous access into a heart and to deliver an implant, a ball joint mechanism configured to connect the delivery system to a delivery station that allows an operator to fix the delivery system within a space around the patient and to manipulate the delivery system in different directions within the target site, a steering mechanism configured to manipulate and to orient the implant within the heart, the steering mechanism configured to pull a steering cable by rotating a steering wheel in order to steer the steerable sheath, a main knob assembly configured to advance and retract a multilumen assembly, a stabilizing tool comprising a plurality of prongs configured to engage the implant within the heart to make an intimate contact with the heart tissue using a stabilizer and a tongue assembly, a back assembly configured to control an actuation mechanism, a suture routing mechanism, a tip lock mechanism, and a back cover configured to protect all sutures.

The steering mechanism may include one or more steering modules configured to pull a steering cable by rotating the steering wheel in order to steer the steerable sheath, a steering shaft comprising a plurality of flat surfaces configured to connect the steering modules and to ensure a rotation alignment, a main knob configured to advance and retract the multilumen inside the delivery system, and a locking mechanism. The actuation mechanism may include a plurality of actuation knobs configured to move along one or more channels and one or more springs configured to maintain tension to the sutures. The suture routing mechanism may include a suture cut configured to separate the suture. The tip handle may be configured to connect to a flushing port to flush and to provide a passage to the guide wire.

BRIEF DESCRIPTION OF DRAWINGS

Aspects, features, benefits and advantages of the embodiments described herein will be apparent with regard to the following description, appended claims, and accompanying drawings where:

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The delivery system may include a steerable sheath configured to provide percutaneous access into a heart and to deliver an implant, a ball joint mechanism configured to connect the delivery system to a delivery station that allows an operator to fix the delivery system within a space around the patient and to manipulate the delivery system in different directions within the target site, a steering mechanism configured to manipulate and to orient the implant within the heart, the steering mechanism configured to pull a steering cable by rotating a steering wheel in order to steer the steerable sheath, a main knob assembly configured to advance and retract a multilumen assembly, a stabilizing tool comprising a plurality of prongs configured to engage the implant within the heart to make an intimate contact with the heart tissue using a stabilizer and a tongue assembly, a back assembly configured to control an actuation mechanism, a suture routing mechanism, a tip lock mechanism, and a back cover configured to protect all sutures.

Figure 1:
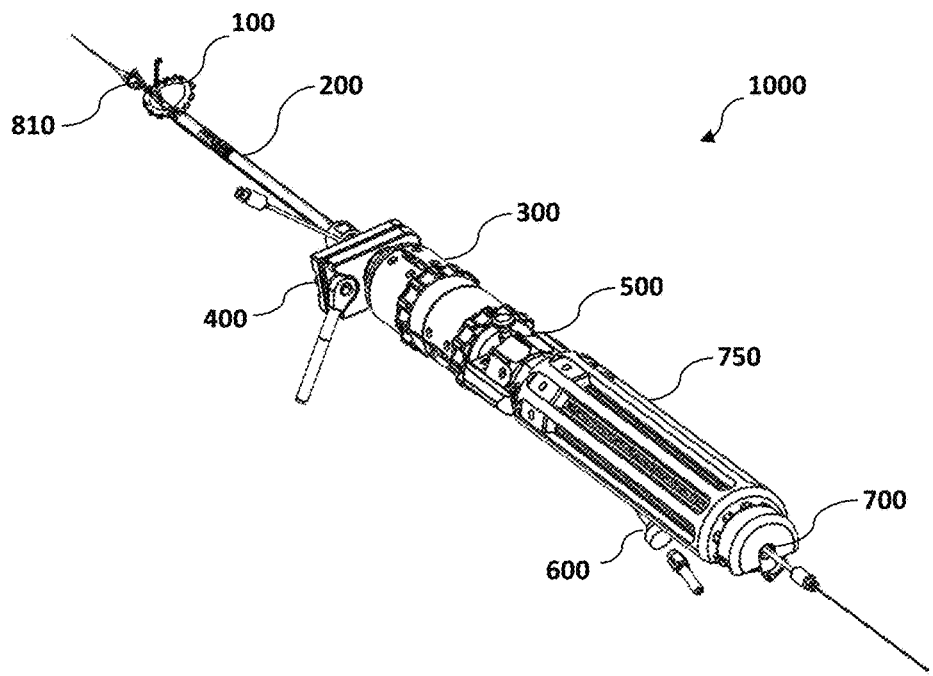
FIG. 1 depicts a perspective view of an illustrative delivery system according to an embodiment.
Figure 2:
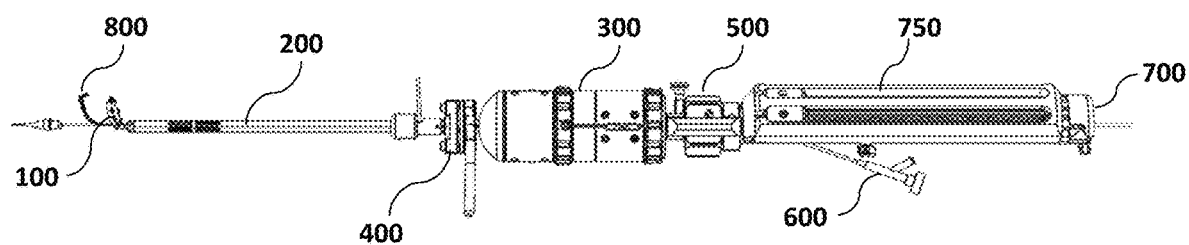
FIG. 2 depicts a detail view of illustrative sections of a delivery system according to an embodiment.

In some embodiments, as shown in FIGS. 1 and 2, the delivery system 1000 may include: an implant 100, a steerable sheath 200, a steering mechanism 300, a ball joint 400, a main knob assembly 500, a hemostat 600, a tip lock mechanism 700, a back assembly 750, and a stabilizing tool 810. Each of these features is discussed in detail herein, with reference to detailed figures.

Figure 3:
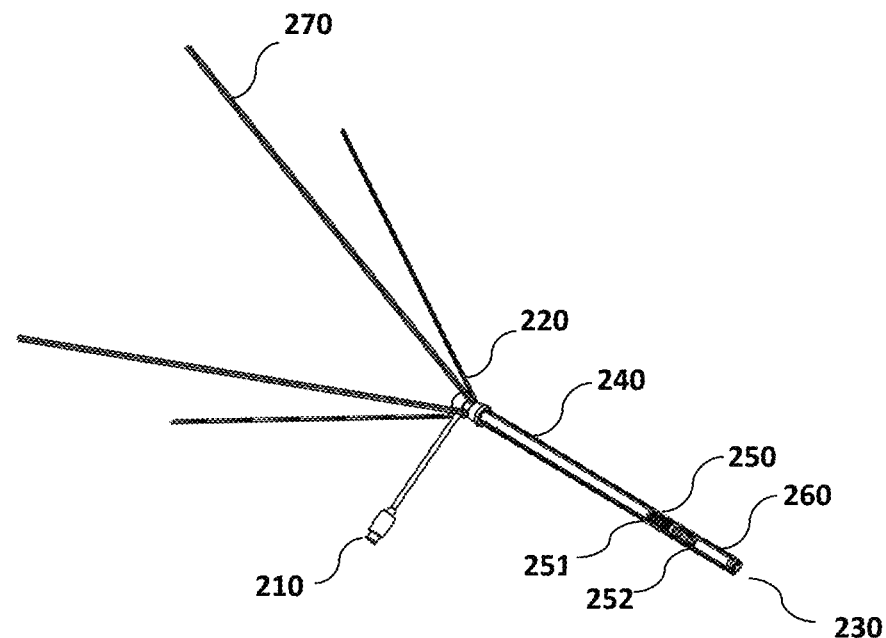
FIG. 3 depicts a detail view of an illustrative steerable sheath according to an embodiment.

The steerable sheath 200, as shown in FIG. 3, is configured to steer in two planes or four directions. The steerable sheath 200 may move along or rotate an implant around a sheath axis, a commissure to commissure axis, and/or an anterior-posterior axis. In some embodiments, the steering directions may be perpendicular to one another. The sheath 230 may be connected to a delivery system at a proximal end 220. The sheath 230 may include a flushing port 210 configured to flush the sheath during a clinical procedure to prevent hemostasis.

Steering may be achieved by pulling one or more steering cables 270 attached to a distal end of the sheath 230. Rotating the steering wheel 331 (FIGS. 11 and 12) moves a steering wire drive 332 (FIG. 12) pulling the respective steering cable. When an operator applies a force, the catheter deflects towards the direction of the force. The implant may rotate around or move along one of the axes as described above due to a bending radius.

Perpendicular steering may be achieved by adding a very rigid element braided with a specifically patterned metal wire. In an embodiment, perpendicular steering may be achieved by coiling and/or braiding a wire around the catheter or adding a hypotube on the outer surface of the sheath 230 with a specific laser cut pattern configured to steer only towards a specific direction.

Steering may also be achieved by using a plurality of flexible segments and a plurality of rigid segments. The location of and distance between two flexible segments, such as 251 and 252, and/or two rigid segments, such as 240 and 260, may vary in ratio between a stroke to a particular direction and a rotation around the axis that is perpendicular to the force. For example, pulling a steering cable/wire in a particular direction may cause the catheter to steer to the particular direction. In such an embodiment, the implant may perform three movements at substantially the same time: a stroke to the particular direction, an inferior movement, and rotation around the axis perpendicular to the particular direction.

Figure 4:
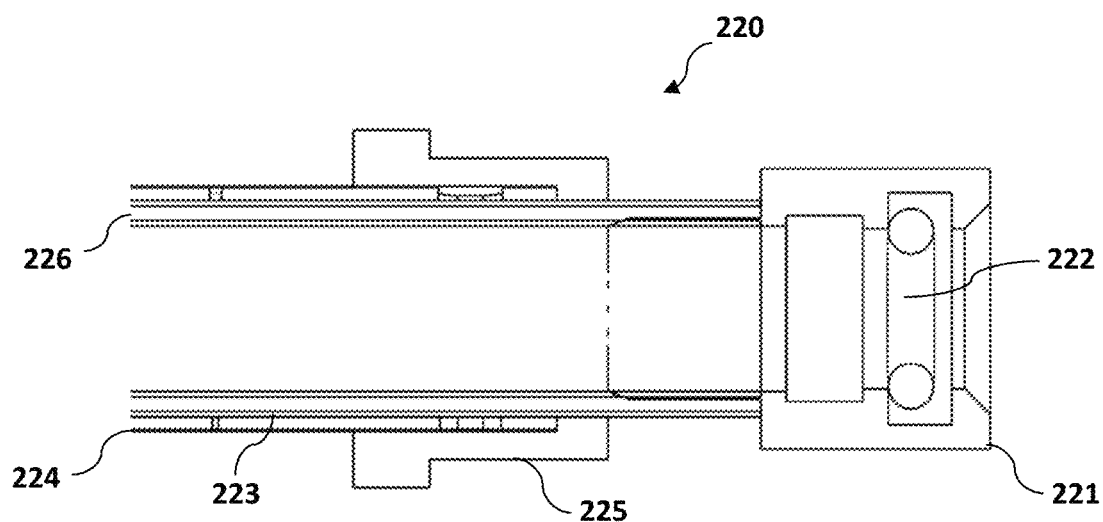
FIG. 4 depicts a cross sectional view of the proximal end of the steerable sheath according to an embodiment.
Figure 5:
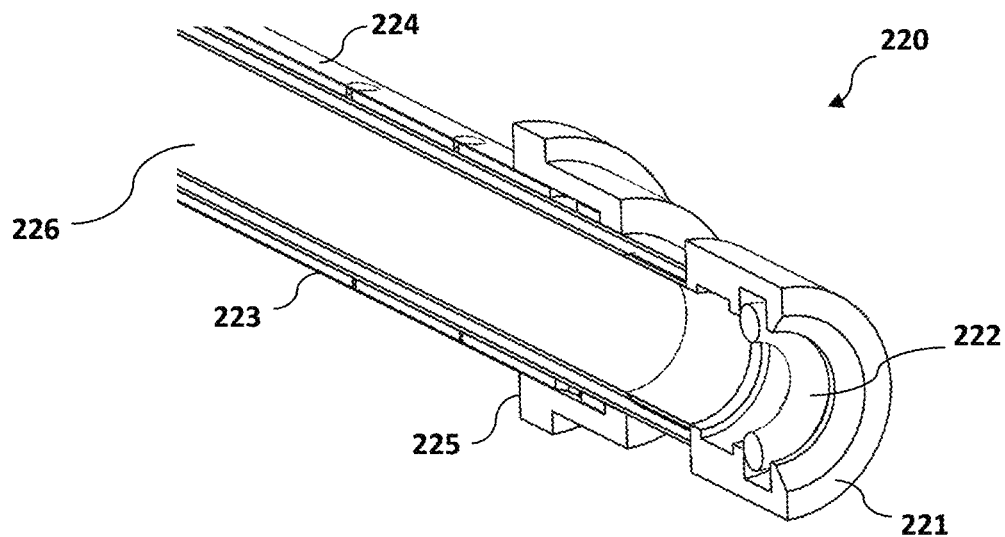
FIG. 5 depicts a cross sectional view of an illustrative proximal sealing of the steerable sheath according to an embodiment.

FIGS. 4 and 5 depict an embodiment of a sealing and connecting mechanism used to connect the sheath to the delivery system handle. A connecting base 225 is configured to tighten the connection to the delivery system by bonding with an adhesive. An O-ring 222 may seal the end of the sheath 230 to prevent fluid from leaking between the inner ID and the catheter that moves within the sheath. In an alternative embodiment, friction between the sealing base 221 and the inner catheter may be used to seal the sheath 230. In yet another embodiment, a septum may be used to seal the sheath 230. Alternative devices for sealing the sheath 230 will be apparent to those of ordinary skill in the art based on this disclosure.

The connecting base 225 may be affixed to the main tube 223 (such as, for example, by pressure, bonding, and/or welding). The sheath extrusion 226 may be attached to the main tube 223, for example, by pressure or bonding. The main tube 223 may be made of, for example, stainless steel, stainless steel/cobalt chrome, a shape memory material (such as, for example, nitinol), or any metal. The pattern on the tube 223 may be machined and/or laser cut, and the surface may be treated with a mechanical surface treatment, such as tumbler, and/or a chemical/electrical surface treatment, such as etching and/or electro-polishing. The sheath extrusion 226 may be a multilumen extrusion with a plurality of lumens. In an embodiment, the sheath extrusion 226 may include at least eight lumens for the steering cables 270. Each of the eight small lumens may be configured to withstand the application of the force, such as about 1,000 newtons (N), without tearing the lumen. Some lumens may include an additional inner lumen comprising, for example, another material to increase material strength. In certain embodiments, a polyimide lumen may be used.

Figure 6:
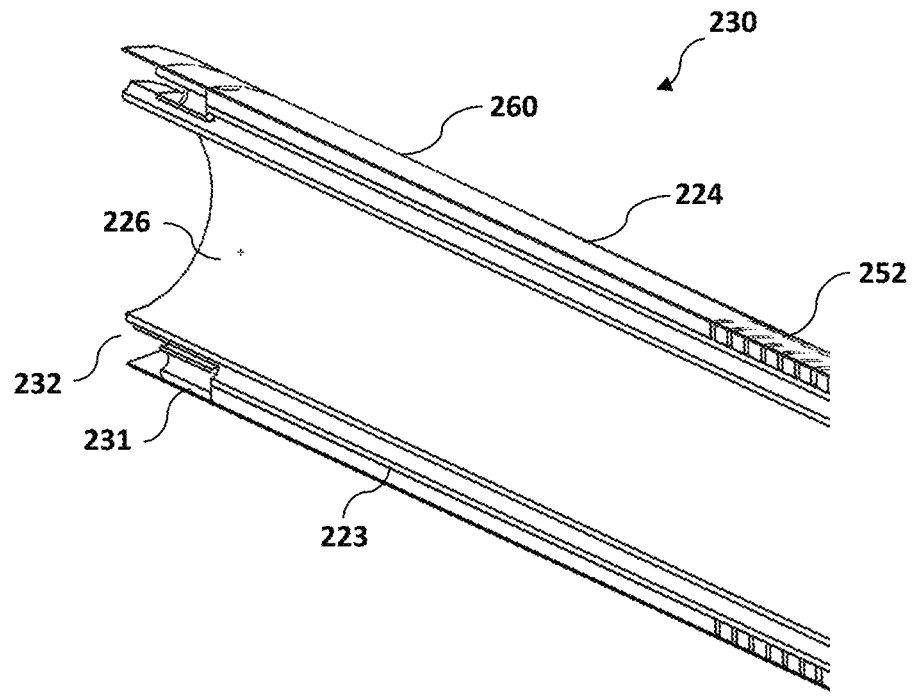
FIG. 6 depicts a cross sectional view of the distal end of the steerable sheath according to an embodiment.

In some embodiments, the steering cables 270 may comprise one or more wires, cables, sutures, rods, bars or other mechanical elements that translate the displacement of the steering modules 330 and 340 (FIG. 8) to the pull ring 231 (FIG. 6) at the distal end of the sheath 230 (FIG. 6). In certain embodiments, the sheath 230 (FIG. 6) may include a heat shrink 224 and/or coating configured to provide a smooth surface with no bumps, holes, or sharp edges. The heat shrink 224 may be made of a hydrophobic material/coating to prevent clotting and thrombosis formation on the sheath components.

Figure 7:
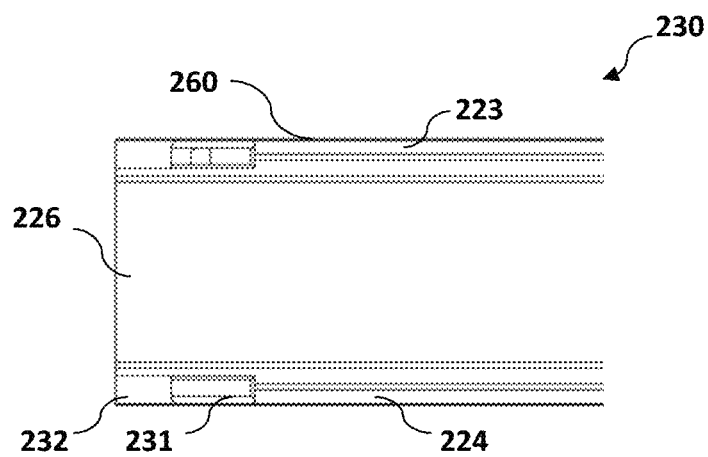
FIG. 7 depicts a cross sectional view of an illustrative pull ring according to an embodiment.

FIGS. 6 and 7 depict an embodiment of the distal end of the sheath 230. In an embodiment, the steering cables/wires 270 (FIG. 1) may be attached to the sheath 230 in a way that allows application of an extremely high force, such as 1,000 newtons (N), without buckling the sheath. In an embodiment, the steering force may be applied to the pull ring 231. The steering cables 270 (FIG. 1) may extend from the sheath 230 to the pull ring 231 through corresponding holes. The pull ring 231 may lean against the main tube of the sheath 223, 260. The heat shrink 224 may be used to prevent blood from leaking between the main tube 223 and the extrusion 226. In an embodiment, a mold 232 of glue (such as, for example, an epoxy, an UV curing, and/or a silicone) may be used to seal the distal end of the sheath 230.

Figure 8:
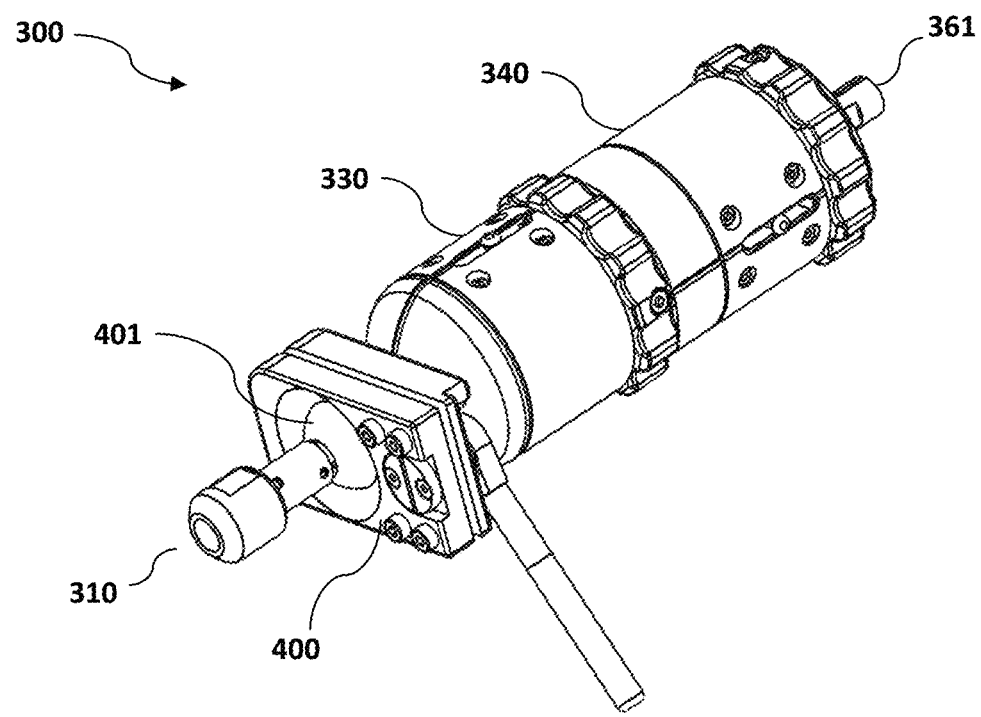
FIG. 8 depicts a perspective view of an illustrative steering mechanism according to an embodiment.

FIG. 8 depicts an exemplary embodiment for a steering mechanism 300 with one or more steering modules 330, 340 assembled in a column and 90 degree rotated to one another along the axis. The steering mechanism 300 may include a steering module 330, 340 for each desired steering plane and/or direction. The steerable sheath 200 may be connected to the distal end of the steering mechanism 310. A distal end of the steering mechanism 310 may be affixed to a ball joint 400 that is an interface to a delivery station. An illustrative delivery station is described in U.S. Provisional Patent Application No. 62/367,190 which is herein incorporated by reference in its entirety.

Figure 9:
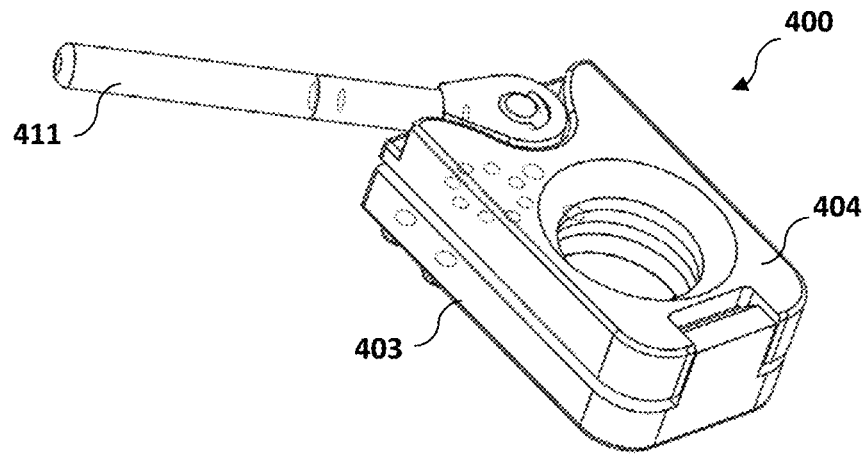
FIG. 9 depicts a detail view of an illustrative ball joint according to an embodiment.
Figure 10:
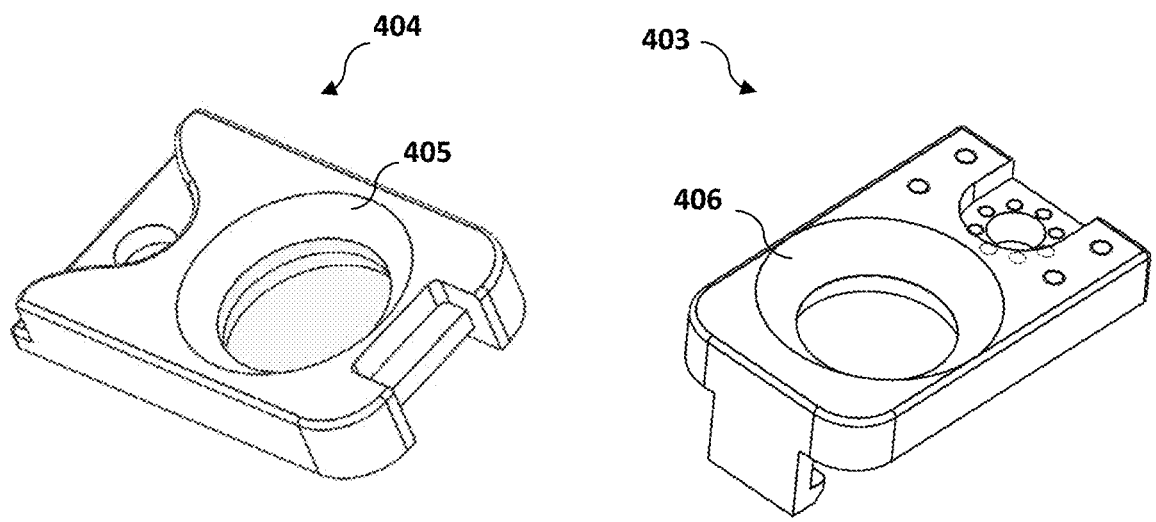
FIG. 10 depicts detail views of illustrative ball joint plates according to an embodiment.

FIGS. 9 and 10 depict an embodiment of a ball joint. As shown in FIG. 9, the ball joint 400 allows the operator to manipulate the orientation of the delivery system within the target site, such as the heart. The ball joint 400 may include a handle 410. The ball joint plates 403 and 404 may include conical surfaces 405 and 406 that are configured to receive a ball on the distal end of a steering shaft in order to provide smooth movement. The ball joint 400 may include materials to allow smooth movement, for example, stainless steel for a ball 401 (FIG. 8) and aluminum/plastic to the ball joint plates 403, 404.

Figure 11:
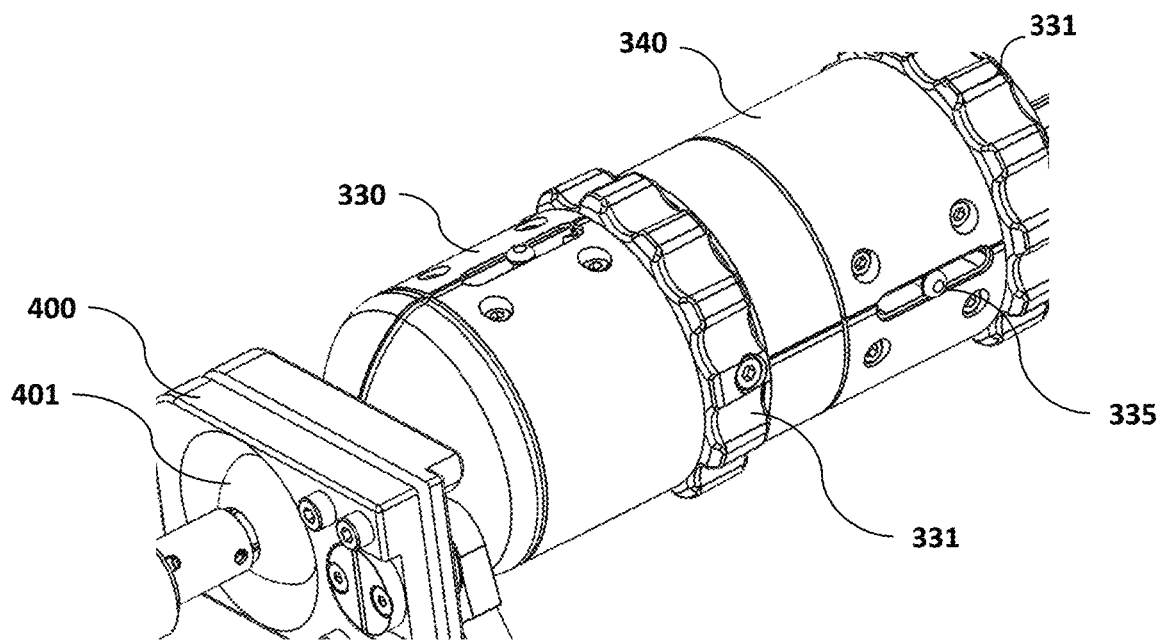
FIG. 11 depicts a perspective view of illustrative steering sections according to an embodiment.
Figure 12:
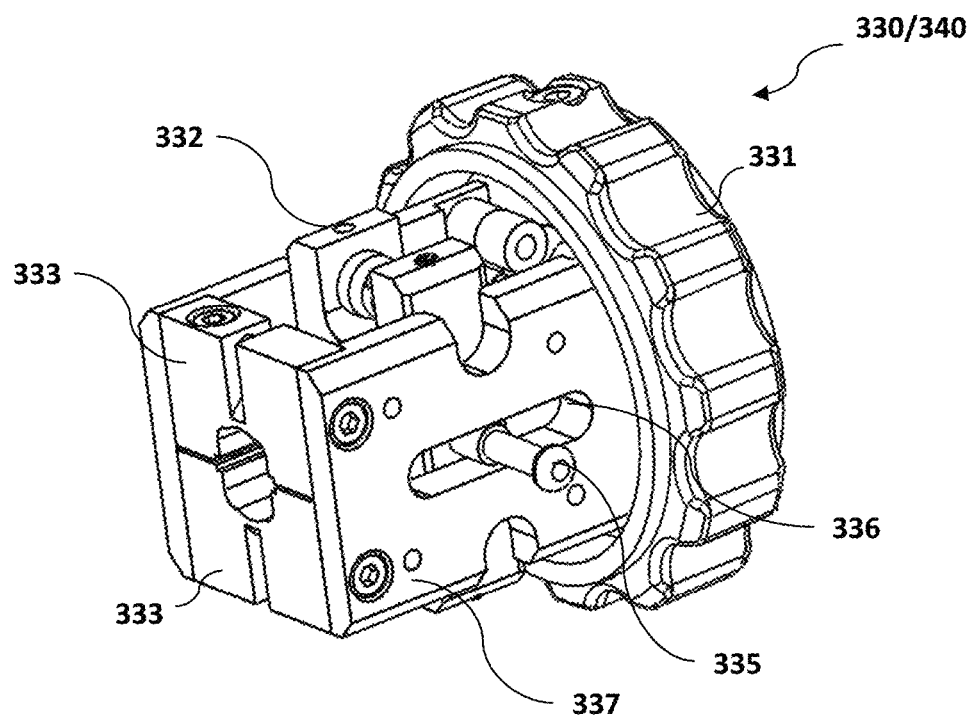
FIG. 12 depicts a detail view of an illustrative steering module according to an embodiment.

As shown in FIGS. 11 and 12, a steering module 330, 340 pulls a steering cable 270 (FIG. 3) by rotating a steering wheel 331. The steering wheel 331 may actuate a steering screw 336 to cause a wire driver 332 to pull the steering cable 270 (FIG. 3). A side wall 337 may prevent the wire driver 332 from rotating. As such, the cable may move only towards the distal end or the proximal end based on the direction of rotation of the steering wheel 331. Guiding components 333 may direct the steering cables 270 (FIG. 3) from the steering shaft 361 (FIG. 8) and ensure that no sharp edges or high angle changes occur in the path of the steering cables.

Figure 13:
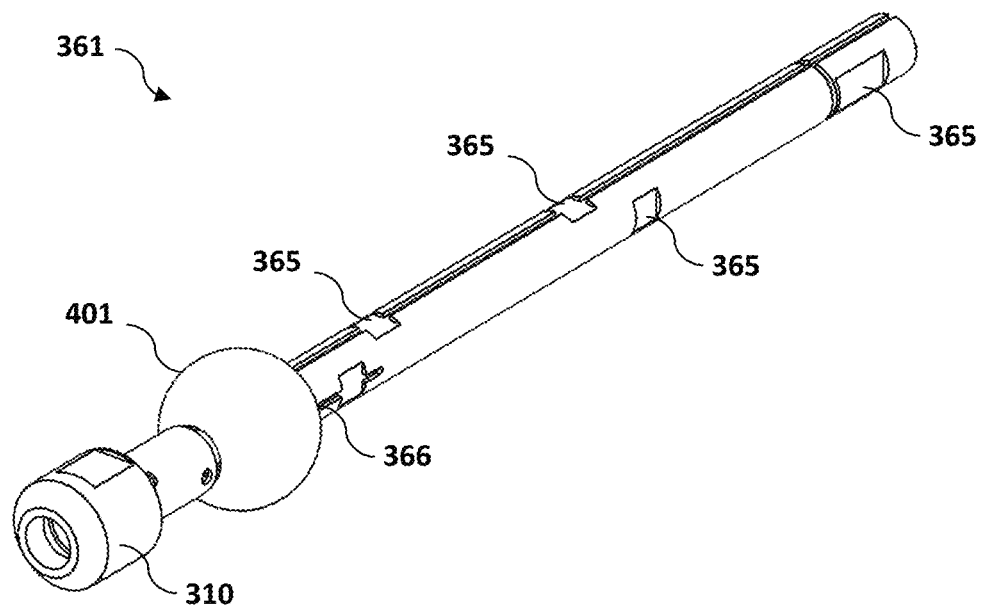
FIG. 13 depicts a detail view of an illustrative steering shaft according to an embodiment.

FIG. 13 depicts an illustrative steering shaft 361. In an embodiment, the steering shaft may include a plurality of flat surfaces 365 configured to position the steering modules 330 and 340 (FIG. 8) accurately and to ensure the rotation alignment among the steering modules. In some embodiments, a distance between adjacent flat surfaces 365 may be between about 30 mm and about 150 mm. The distance between adjacent flat surfaces 365 may influence the length of the steering mechanism 300 (FIG. 8) and the steering stroke. The relative orientation between the flat surfaces may determine the direction in which sutures are pulled so that each of the one or more steering modules 330, 340 (FIG. 8) may be positioned in any relative orientation that is required. The steering shaft 361 may include four cable tunnels 366 configured to ensure safe passage of the sutures from the sheath to the required steering modules 330 and 340 (FIG. 8).

Figure 14:
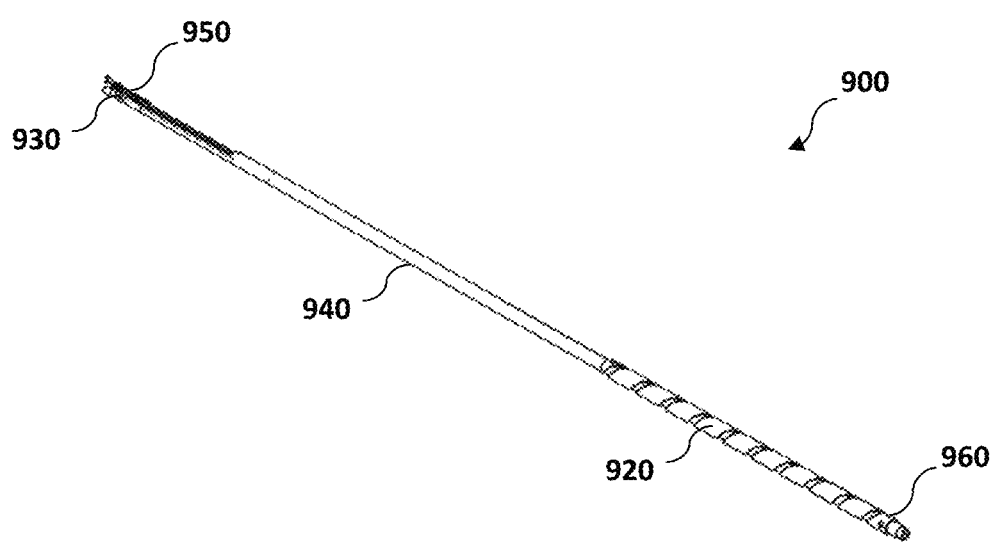
FIG. 14 depicts a detail view of an illustrative multilumen (ML) shaft according to an embodiment.
Figure 37:
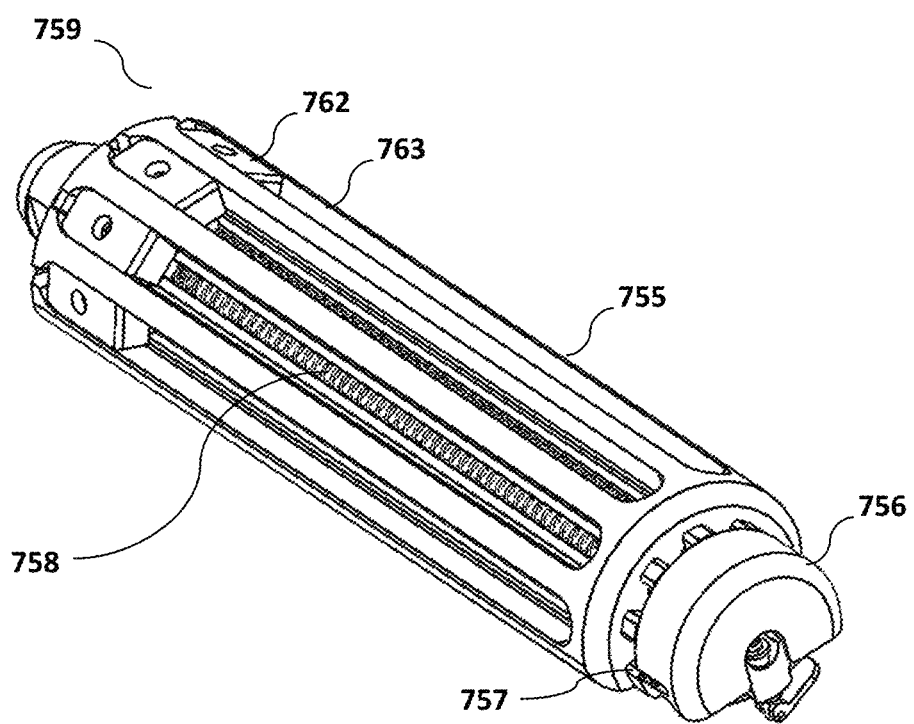
FIG. 37 depicts a detail view of an illustrative back module for a delivery system according to an embodiment.
Figure 38:
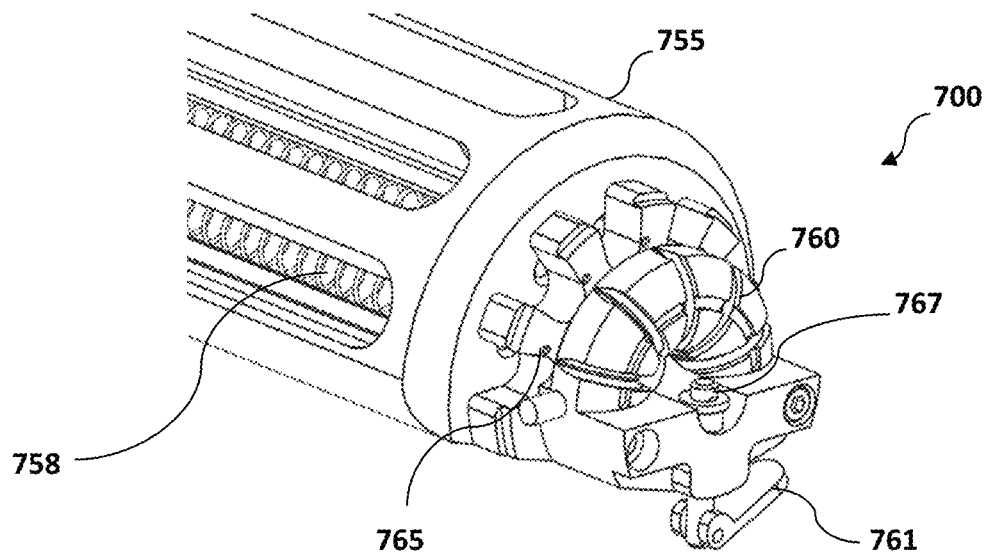
FIG. 38 depicts a detail view of an illustrative proximal end for a back module according to an embodiment.
Figure 39:
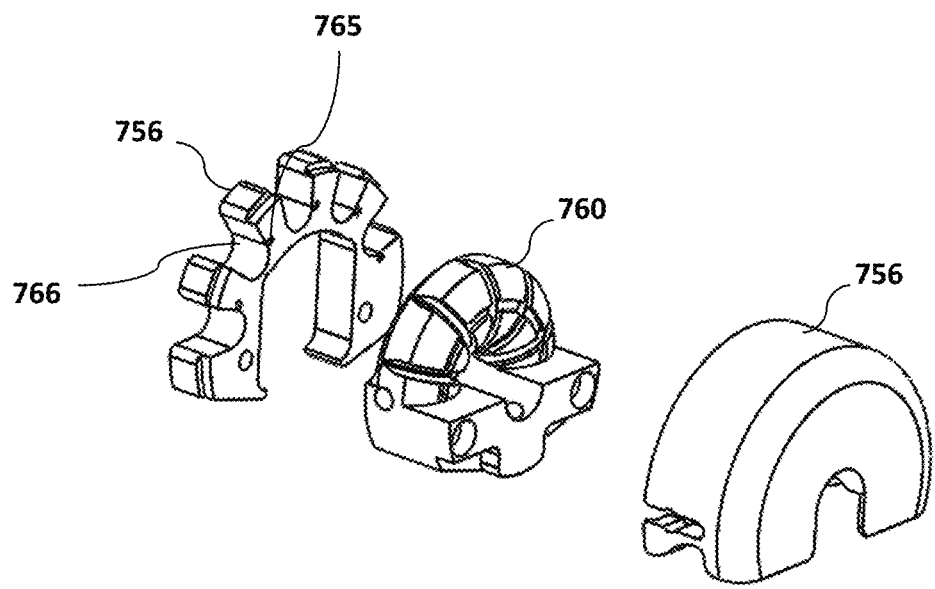
FIG. 39 depicts a detail view of an illustrative suture routing according to an embodiment.
Figure 40:
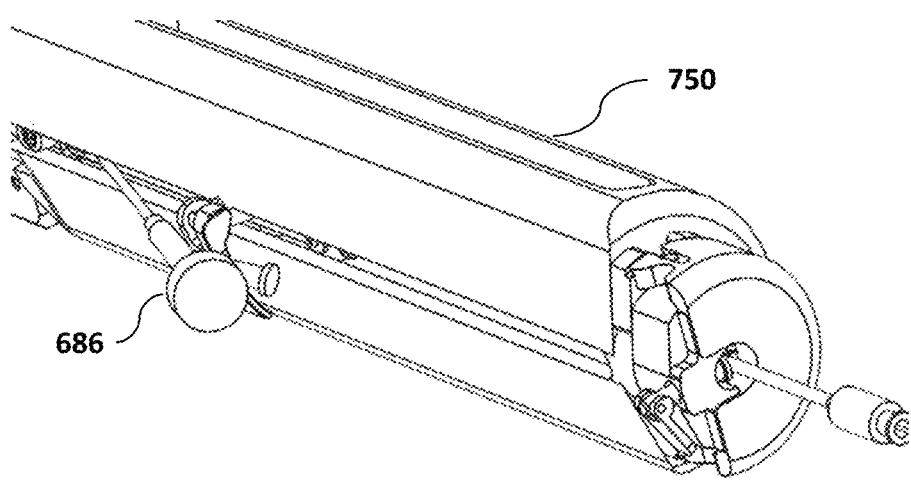
FIG. 40 depicts a detail view of an illustrative back assembly according to an embodiment.

FIG. 14 depicts an exemplary embodiment of the ML shaft 900. The ML shaft 900 may be a catheter moving through the sheath 200 (FIGS. 1 and 2) and the steering mechanism 300 (FIGS. 1 and 2). The ML shaft 900 may be connected with the implant at a distal end 950 and an actuation mechanism 759 (FIG. 37) at a proximal end 960.

Figure 15:
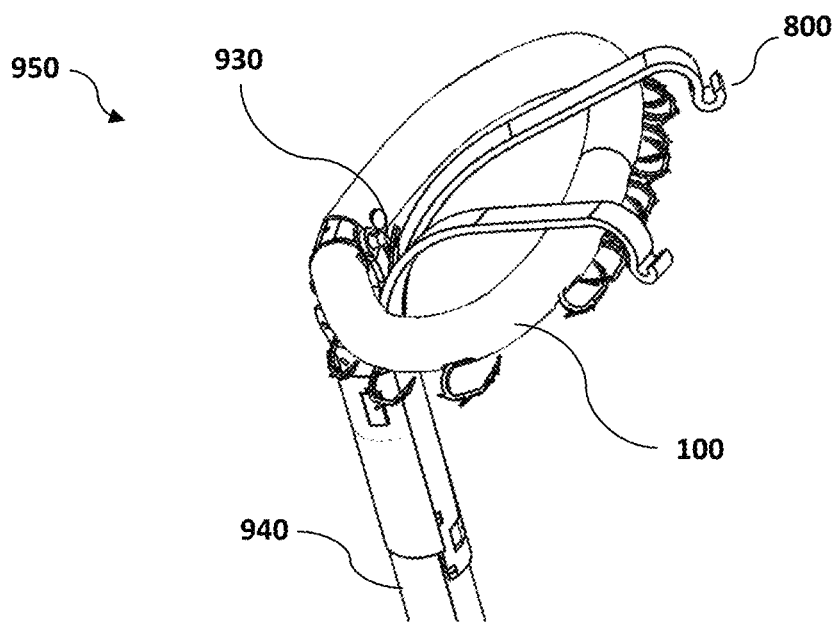
FIG. 15 depicts a detail view of an illustrative implant mounted onto the delivery system according to an embodiment.

FIG. 15 shows an embodiment for the distal end of the ML shaft 950 when the implant is mounted and in a deployed configuration. The distal end of the ML shaft 950 may include a multilumen extrusion along with a metallic backbone 940 for a structural stiffness and an interface assembly including the stabilizer 938 (FIG. 16), the tongue assembly 930, and the stabilizing tool 800.

Figure 16:
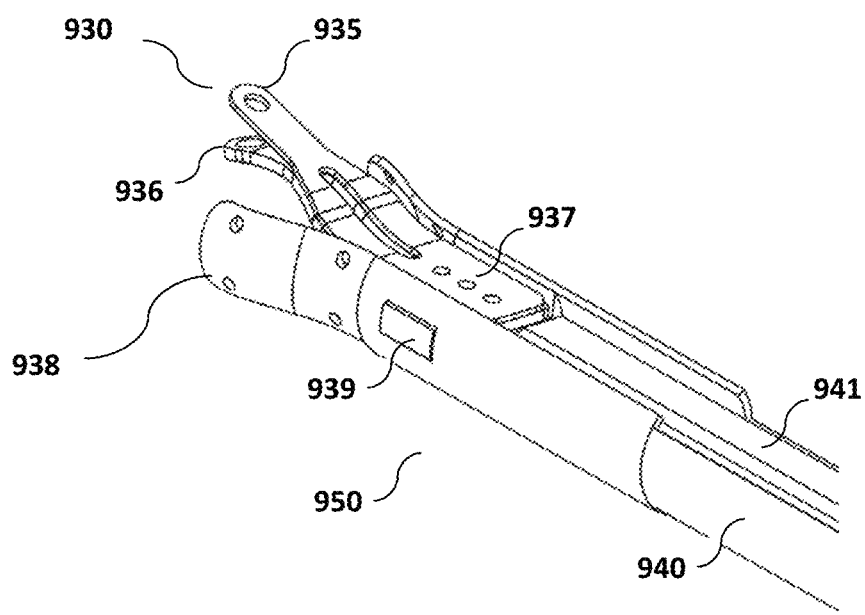
FIG. 16 depicts a detail view of an illustrative implant interface of the delivery system according to an embodiment.
Figure 17:
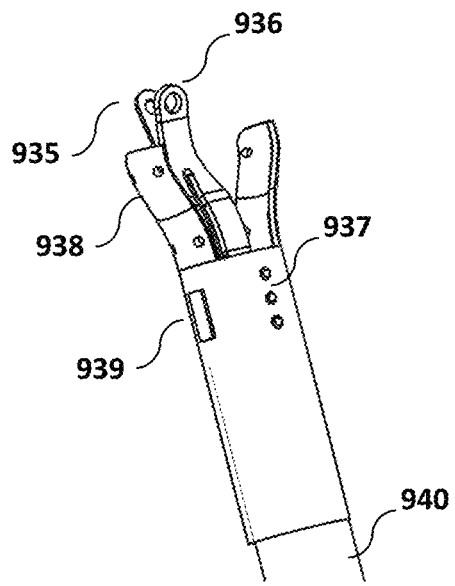
FIGS. 17 and 18 depict detail views of an illustrative stabilizer and an illustrative tongue assembly according to an embodiment.
Figure 18:
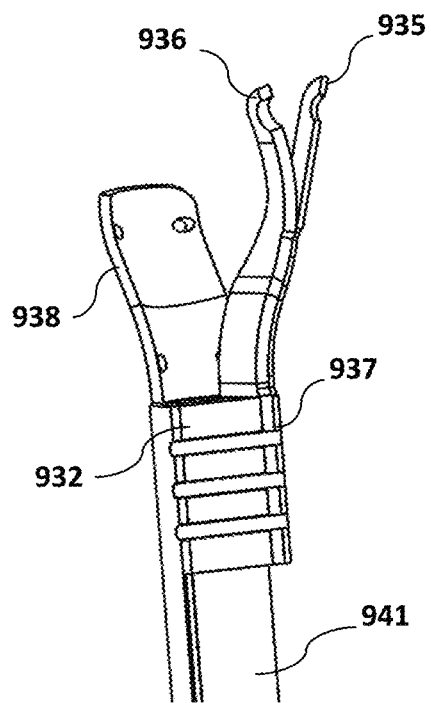

FIGS. 16, 17, and 18 show an exemplary embodiment for the stabilizer 938 and the tongue assembly 930. In an embodiment, the stabilizer 938 and the tongue assembly 930 may be mounted on a distal end of the ML shaft 950. The stabilizer 938 may be configured to provide stabilization for the implant 100 (FIGS. 1 and 2) during actuation. The tongue assembly 930 may provide a connection interface with the implant 100 (FIGS. 1 and 2). The stabilizer 938 and the tongue assembly 930 may be attached through a ML head 932 which may be a metal/plastic machined, molded, and/or printed part. The ML stage 939, as a part of the ML head 932, is configured to provide a mechanical attachment to the stabilizer 938. Ports for pins 937 are configured to attach the tongue assembly 930 to the stabilizer 938 through the ML head 932. The pins 937 may be affixed to the tongue assembly 930 and/or to the stabilizer 938 by, for example, an interference connection, bonding, and/or welding. The stabilizer 938 may be attached to the multilumen by bonding to the ML extrusion 941 and the metallic backbone 940 in order to provide a continuous metallic structure.

The tongue assembly 930 may include one or more tongues. In some embodiments, the tongue assembly 930 may be made of nitinol or any other metallic material. A tongue may be affixed to another tongue by, for example, a mechanical attachment, bonding, and/or welding. In various embodiments, the tongue assembly 930 may include different geometries at the distal ends 935 and 936 to achieve a spring effect. When engaging the implant, the distal ends 935 and 936 of the tongue assembly 930 may overlap with a pin. Once the wire is removed, the tongue 935 jumps outside of the pin due to a spring effect, and the tongue 936 may easily be released from the pin. In other embodiments, the tongue 935 and 936 may include the same or different size holes to achieve an easy release of the tongues from the pin. In a particular embodiment, the tongue 936 may have a larger hole diameter than a pin diameter. In certain embodiments, the tongue 935 may include a clearance hole to hold the pin strongly and to be released based on the spring effect. In various embodiments, the tongue 935 may have a thickness configured to support the desired geometry and strength of the spring effect.

Figure 19:
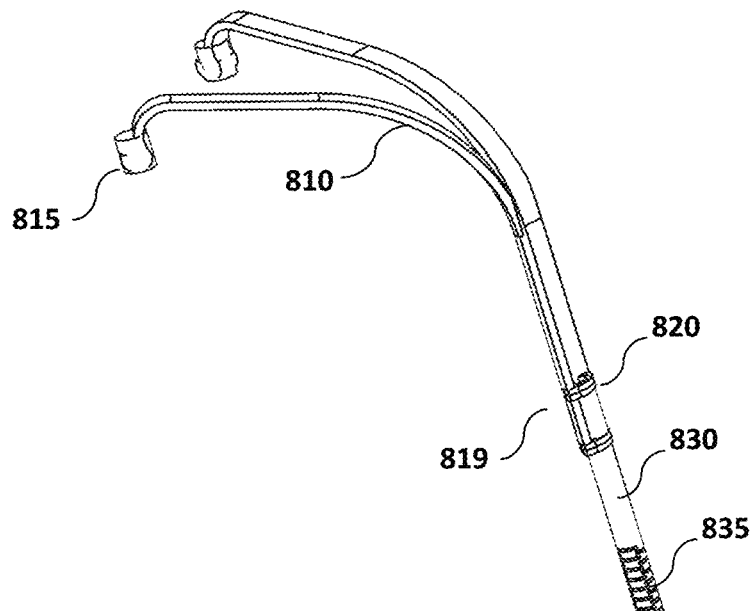
FIG. 19 depicts a detail view of an illustrative stabilizing tool according to an embodiment.
Figure 20:
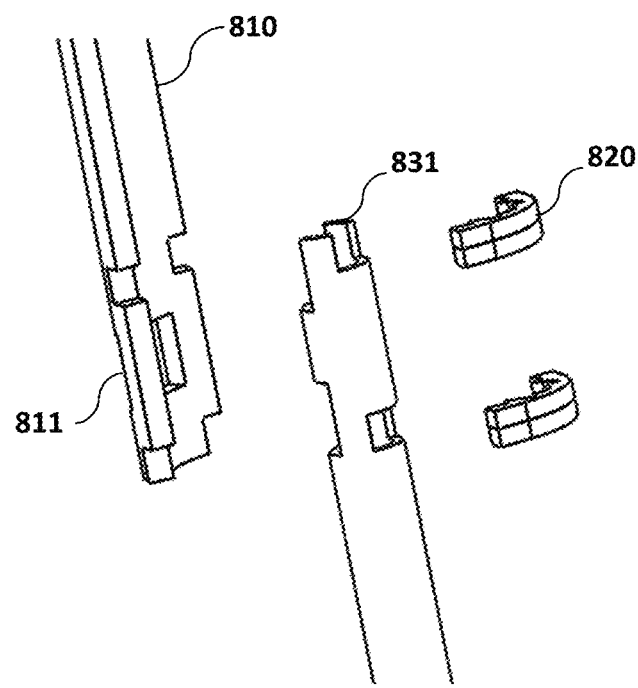
FIG. 20 depicts a detail view of an illustrative stabilizing tool attachment according to an embodiment.

FIGS. 19 and 20 show illustrative embodiments of the stabilizing tool 810 and a plurality of stabilizing tool attachments 819. The stabilizing tool 810 may include a plurality of prongs. The stabilizing tool 810 may be configured to engage the implant within the heart to make an intimate contact with the heart tissue while manipulating and anchoring the implant towards a particular orientation. The distal end of the stabilizing tool 810 may be manufactured by laser cutting with a specific pattern and may be shaped with a heat treatment process. In some embodiments, the stabilizing tool 810 may include a soft material 815, such as, for example, silicon using a molding or other bonding process. The stabilizing tool may be manufactured from a variety of materials including, for example, stainless steel, cobalt chrome, nitinol, shape memory alloys, and other biologically compatible materials by machining, laser cut, and/or molding.

A stabilizing tool attachment 819 may be a combination of a mechanical joint, bonding, and/or welding to provide material strength. The stabilizing tool attachment 819 may be attached to the rod 830 through the distal end of the rod 831. The distal end of the rod 831 may be machined or laser cut to a shape that interacts with corresponding slots on the proximal end of the stabilizing tool 811 and additional plates 820. In some embodiments, combining the proximal end of the stabilizing tool 811, the distal end of the rod for the stabilizing tool 830, and the plates 820 may provide maximal strength without relying on bonding and/or welding. The rod 831 of the stabilizing tool 830 may include a flexible segment 835 to allow steering of the multilumen without decreasing the sheath steering performance.

Figure 21:
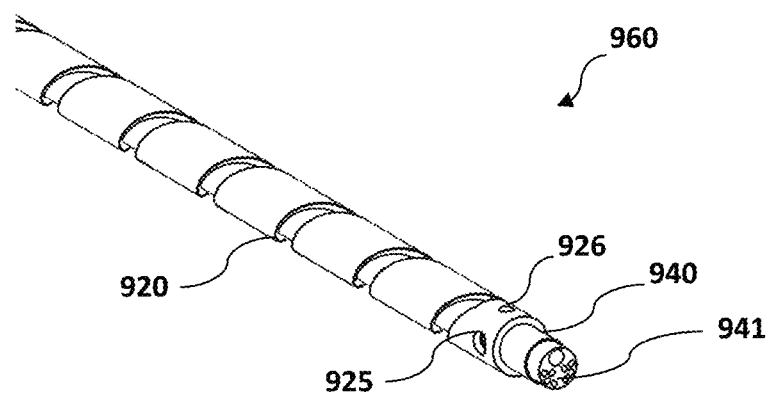
FIG. 21 depicts a detail view of an illustrative multilumen thread according to an embodiment.
Figure 22:
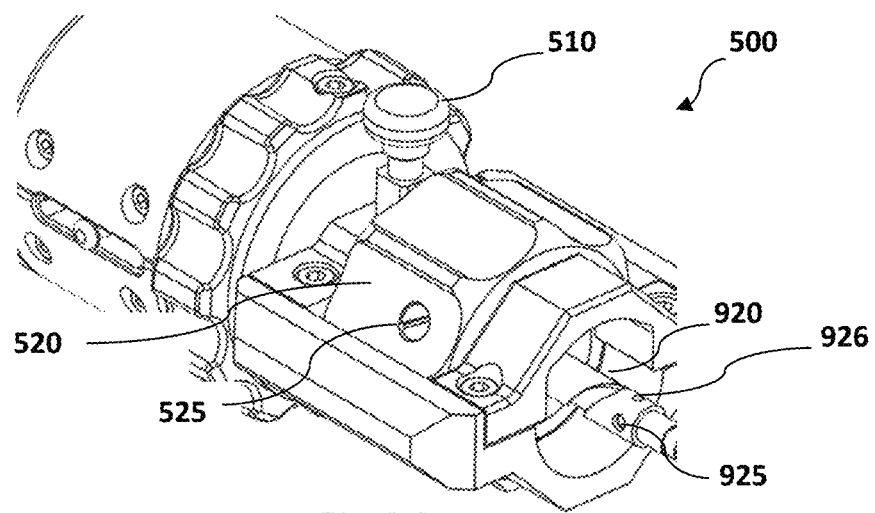
FIG. 22 depicts a detail view of an illustrative implant advance knob according to an embodiment.
Figure 23:
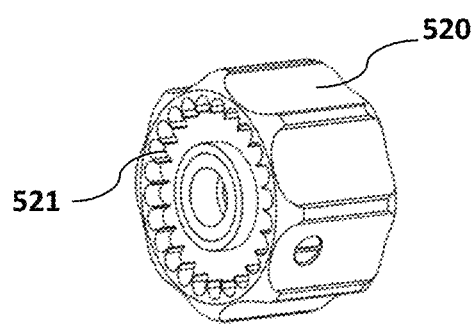
FIGS. 23 and 24 depict detail views of an illustrative discrete lock mechanism according to an embodiment.
Figure 24:
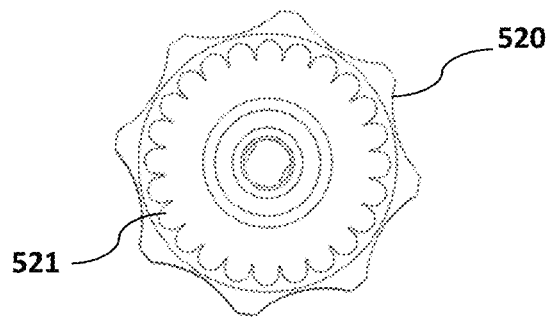
Figure 25:
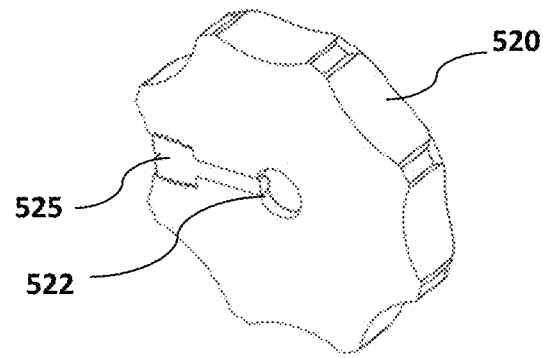
FIG. 25 depicts a detail view of an illustrative main knob according to an embodiment.
Figure 26:
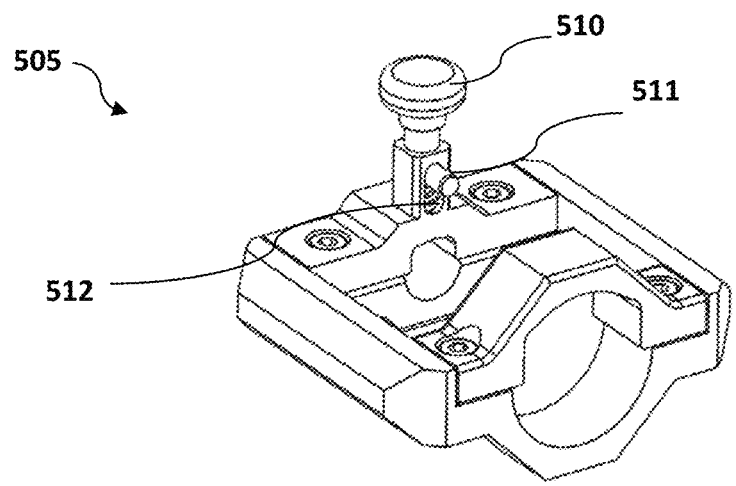
FIG. 26 depicts a detail view of an illustrative locking mechanism of a main knob according to an embodiment.
Figure 27:
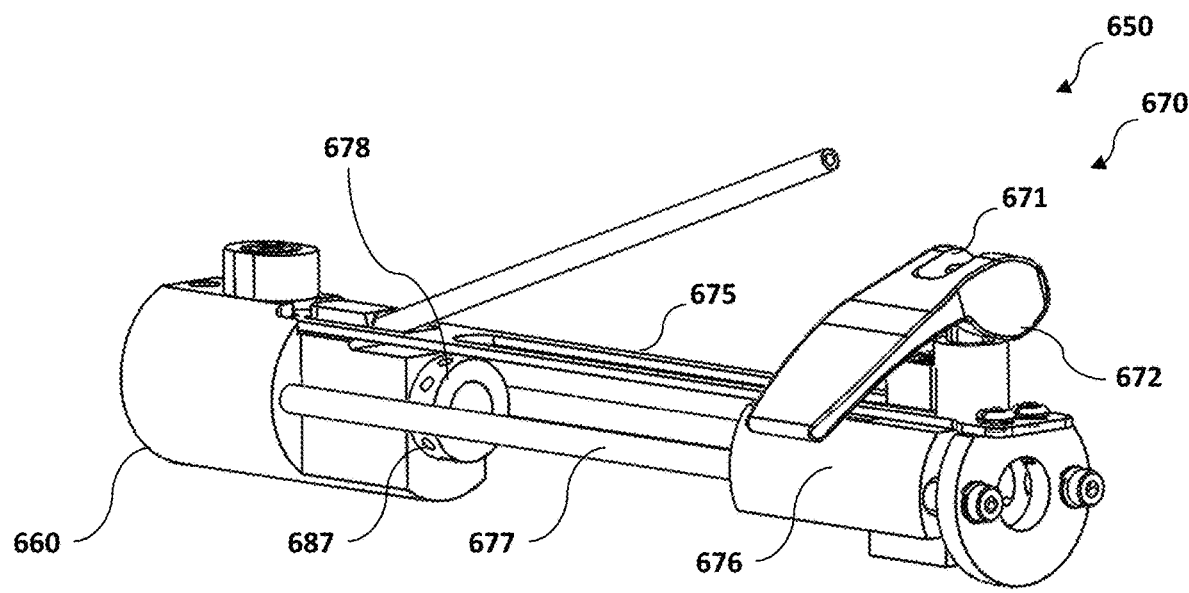
FIGS. 27 and 28 depict detail views of an illustrative stabilizing tool handle and an illustrative lock according to an embodiment.
Figure 28:
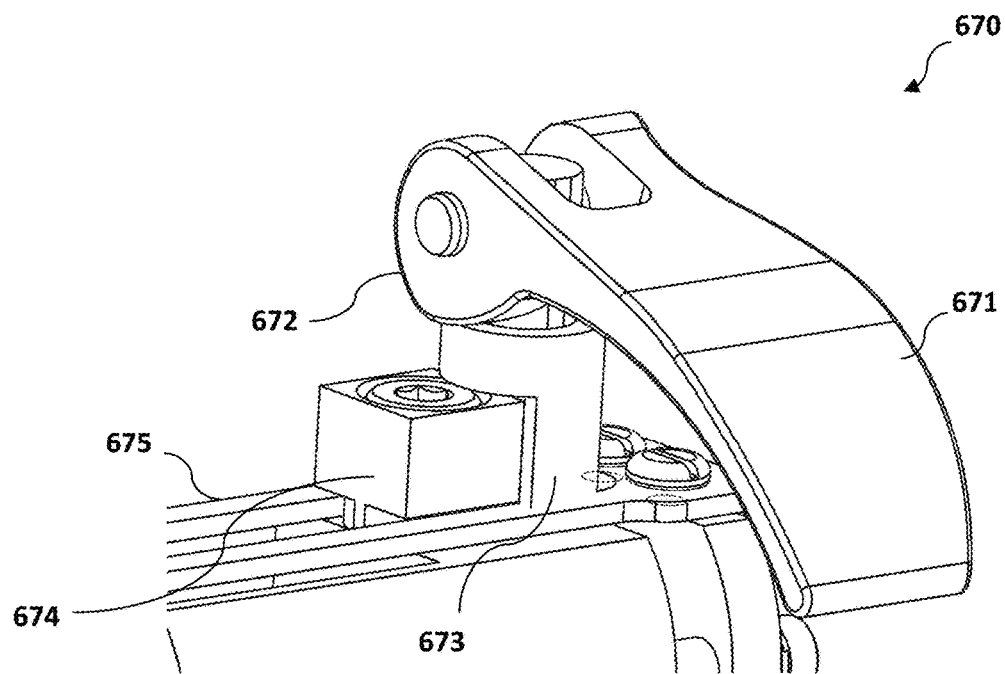
Figure 29:
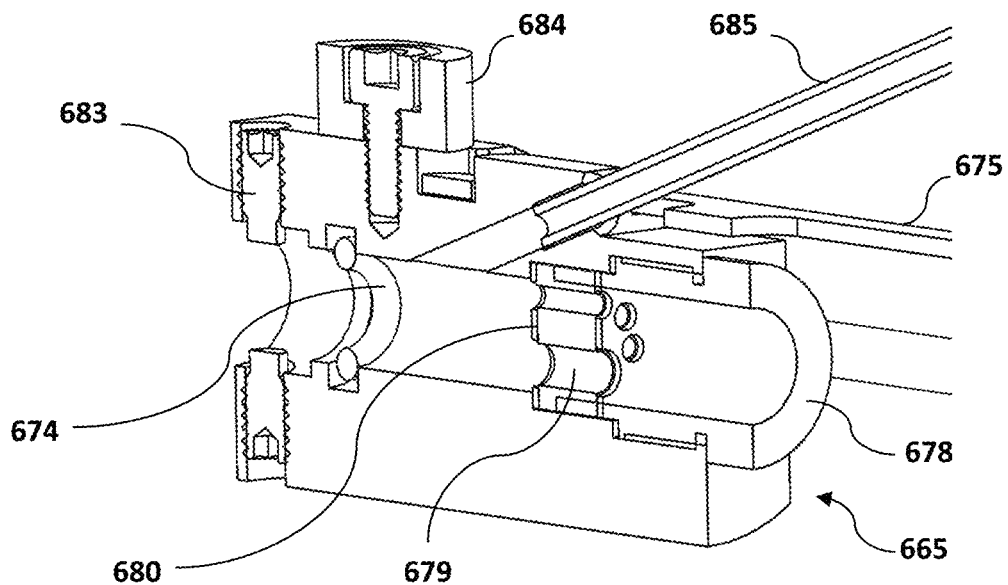
FIG. 29 depicts a detail view of an illustrative multilumen sealing and flushing according to an embodiment.
Figure 30:
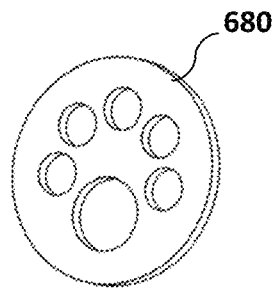
FIG. 30 depicts a view of an illustrative sealing plate according to an embodiment.

FIG. 21 depicts an embodiment of the proximal end of the multilumen 960. The proximal end of the multilumen 960 may include an interface with an main knob assembly 500 (FIG. 22). The proximal end of the multilumen 960 may include the backbone 940 and a threaded tube 920. In some embodiments, the threaded tube 920 may be separately manufactured by laser cutting, machining, bonding, and/or welding to the backbone 940. In an embodiment, all of the components may be manufactured from one piece. The threaded tube 920 may include keying features 925, 926 configured to align the backbone 940 to the steering mechanism 300 (FIG. 8) and to the delivery system.

FIGS. 22-26 show various embodiments of the main knob 520 for the delivery system. The main knob 520 is configured to advance and retract the implant inside the delivery system. Typically, the main knob 520 is in a normally closed configuration to ensure that the operator cannot move the multilumen thread accidentally. A locking mechanism 505 may include a locking button 510 that is configured to lock the main knob 520 by pushing a main knob locking pin 511 into a slot 521 of the main knob 520. The slots 521 may be configured to lock the main knob 520 in a discrete position. In some embodiments, locking the main knob 520 may be performed by creating friction or the like. The force of the lock may be determined by a spring 512. The advancement of the multilumen 900 (FIG. 14) is done by one or more pins 525 that protrude from the main knob 520. The pins 525 may be affixed to the main knob 520 by threads, bonding, and/or welding, and the height of the protrusion may vary by design.

FIGS. 27-35 show various embodiments of an illustrative ML cart 676. The ML cart 676 may be a subassembly configured to control the stabilizing tool 800 and to enable sealing and flushing of the multilumen 900 catheter. The ML cart 676 may include a sealing mechanism 665, a stabilizing tool handle 670, a stabilizing tool lock rail 675, and one or more ML cart rails 677 for the stabilizing tool handle 670. The stabilizing tool handle 670 may include an actuation knob 671 configured to open and lock the handle to the ML cart 676 through the locking mechanism. Locking may be achieved by pushing the lock cylinder 673 on the lock block 674 against the stabilizing tool lock rail 675. The lock contour 672 of the actuation knob 671 may be used to alter the amount of force required to lock and release the actuation knob. The one or more ML cart rails 677 may enable smooth movement of the stabilizing tool 800 by guiding the handle 670 forwards and backwards.

Figure 31:
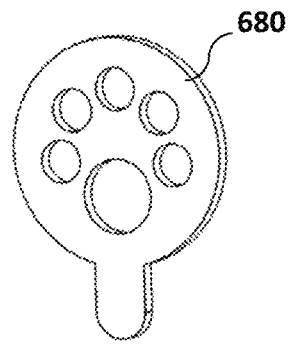
FIG. 31 depicts a view of an illustrative seal plate according to an embodiment.
Figure 32:
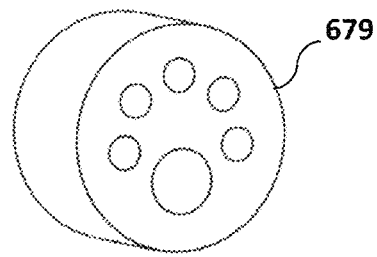
FIG. 32 depicts a view of an illustrative seal septum according to an embodiment.
Figure 33:
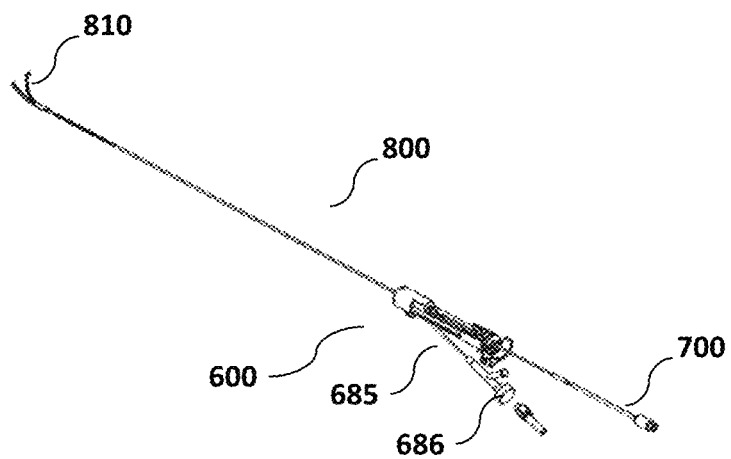
FIGS. 33-35 depict perspective views of an illustrative stabilizing tool attachment according to an embodiment.
Figure 34:
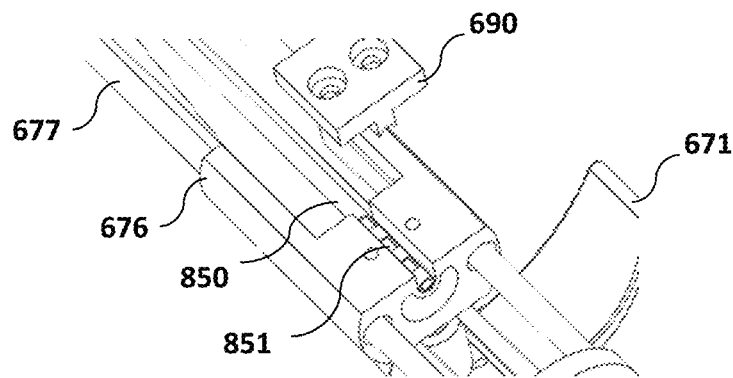
Figure 35:
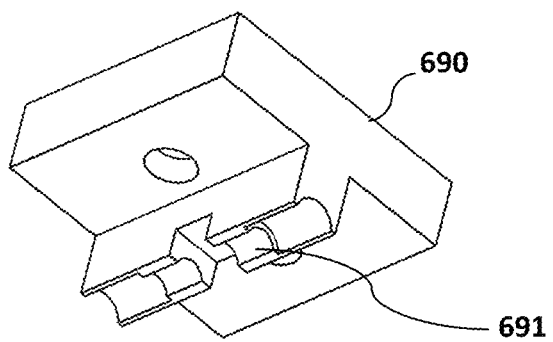

In various embodiments, the sealing mechanism 665 may be configured to enable flushing of all lumens in the catheter and to prevent blood from seeping backwards during the procedure (for example, by hemostasis). The sealing mechanism 665 may be positioned within the multilumen base 660. A septum 679 may be compressed by two metal plates 680. The metal plates 680 may centralize the sutures, rods, and/or wires that pass through the holes in the septum 679 and plates. In addition, the metal plates 680 may provide uniform pressure on the septum 679 to achieve optimal sealing. The ML screw 678 may impart pressure on the metal plates 680 and may include one or more holes 687 that are configured to be tightened or loosened. In some embodiments, the ML base 660 may include a flushing port 685 that may be attached to a hemostat 686. In an embodiment, the metal plates 680 may include a keying feature, as shown in FIG. 31, to prevent rotation of the metal plates and to apply shear forces onto the sutures that pass through the plates and septum.

The ML cart 676 may be attached to the stabilizing tool assembly 800 at the proximal end of the stabilizing tool 850. In various embodiments, the stabilizing tool assembly 800 may include a specific pattern 851 that may be machined or laser cut. The pattern 851 may be configured to enable a mechanical attachment of the rod to the ML cart 676 using a bipod cover 690. In some embodiments, the bipod cover 690 may include a pattern 691 corresponding to the pattern 851 of the stabilizing tool assembly 800. The one or more ML cart rails 677 may include a low friction coating and/or may be manufactured from metal and/or plastic. In some embodiments, a low friction liner may be added between the one or more ML cart rails 677 and the ML cart 676.

Figure 36:
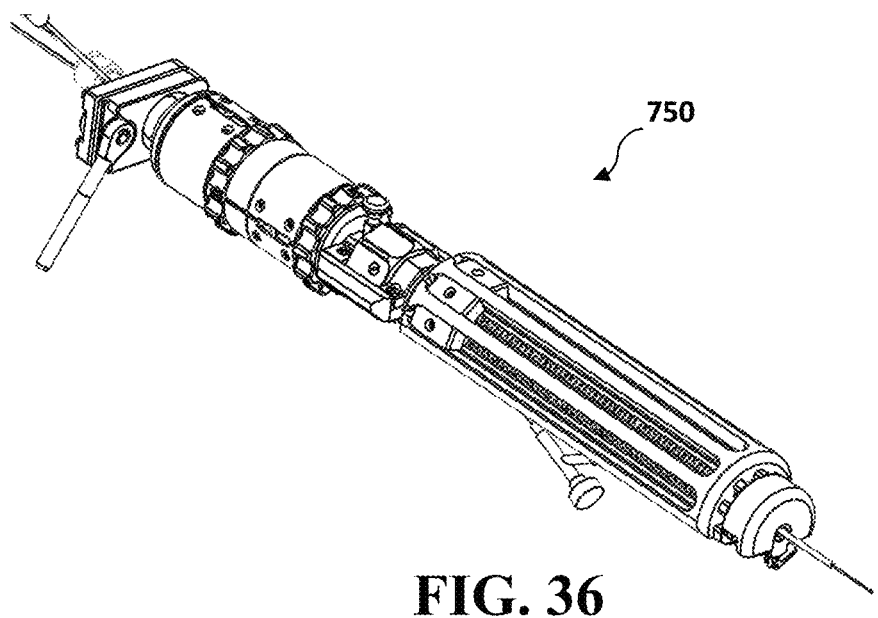
FIG. 36 depicts a perspective view of an illustrative back assembly for a delivery system according to an embodiment.

FIG. 36 shows a perspective view of an illustrative back assembly. FIGS. 37-40 also show illustrative embodiments for the back assembly of the delivery system. The back assembly 750 may include an actuation mechanism 759, a suture routing mechanism, and a tip lock mechanism 700. In some embodiments, the actuation mechanism 759 may include a plurality of actuation knobs 762 configured to move along one or more channels 763 that are located inside of the back assembly module 755. In various embodiments, the one or more channels 763 may include one or more springs 758 configured to maintain tension to the sutures. Each suture may extend from the implant through the multilumen, reverse its direction at a suture rotation part 760, and be attached to the actuation mechanism 759. The suture path may or may not include a suture cut 757 that enables a separation between suture pairs.

Each actuation may include one suture that runs from the actuation mechanism 759 through the multilumen to the implant and comes back through the same path. If the operator desires to cut only one end of the suture, the suture path may protect the suture from being cut by mistake by passing one of the ends through a plurality of holes 765 and the corresponding end in the free path 766. The back cover 756 may be configured to protect all of the sutures together or separately. In other embodiments, the back cover 756 may include several sub components that can separate and dispose of some of the sutures.

Some embodiments may include the tip lock mechanism 700 configured to lock a tip lock 767 at the proximal end of the back assembly 750. A tip lock handle 761 locks the tip lock 767 that runs through the tip lock mechanism 700 and the stabilizing tool 800 from the proximal end to the distal end of the delivery system and connects a tip to the tip lock. In other embodiments, a flushing port may be placed at the proximal end of the tip lock 767. The flushing port may be configured to flush the tip lumen and provide a passage to the guide wire.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A delivery system for percutaneous heart valve repair, the delivery system comprising:
   a steerable sheath configured to provide percutaneous access into a heart and to deliver an implant;
   a steering mechanism configured to manipulate and orient the implant;
   a ball joint mechanism configured to connect the steerable sheath to the steering mechanism;
   wherein the steering mechanism is further configured to pull a steering cable by rotating a steering wheel in order to steer the steerable sheath, the steering mechanism comprising:
     one or more steering modules, and
     a steering shaft comprising a plurality of flat surfaces configured to connect the one or more steering modules and to ensure a rotational alignment;
   a main knob assembly configured to advance and retract a multilumen shaft assembly, wherein the multilumen shaft assembly comprises a multilumen shaft configured to connect to the implant on a distal end and to an actuation mechanism on a proximal end;
   a stabilizing tool comprising a plurality of prongs configured to engage the implant within the heart to make an intimate contact with the heart tissue using a stabilizer and a tongue assembly, wherein the stabilizing tool is configured to be controlled by a multilumen cart, wherein the multilumen cart is configured to enable sealing and flushing of the multilumen shaft; and
   a back assembly comprising:
     the actuation mechanism;
     a suture routing mechanism;
     a tip lock mechanism; and
     a back cover configured to protect all sutures being cut by mistake.

2. The delivery system of claim 1, wherein the steerable sheath comprises a rigid element braided with a specifically patterned metal wire.

3. The delivery system of claim 1, wherein the steerable sheath comprises a wire coiled around the steerable sheath.

4. The delivery system of claim 1, wherein the steerable sheath comprises a hypotube on an outer surface of the sheath.

5. The delivery system of claim 1, wherein the steerable sheath comprises a heat shrink and a pull ring.

6. The delivery system of claim 1, wherein the steerable sheath is connected to a multilumen base comprising a flushing port configured to be attached to a hemostat.

7. The delivery system of claim 1, wherein the steerable sheath has a sheer strength of about 1,000 newtons (N).

8. The delivery system of claim 1, wherein the multilumen shaft comprises a multilumen extrusion, a metallic backbone, an interface assembly, the stabilizer, the tongue assembly, and the stabilizing tool.

9. The delivery system of claim 1, wherein the steering shaft comprises a plurality of flat surfaces, wherein a distance between adjacent flat surfaces is in a range from about 30 mm to about 150 mm.

10. The delivery system of claim 1, wherein the steering shaft comprises a flat surface configured to determine a steering stroke and a steering direction.

11. The delivery system of claim 1, wherein the stabilizing tool comprises a flexible segment configured to steer the multilumen shaft.

12. The delivery system of claim 1, wherein the ball joint mechanism comprises:
    a handle; and
    a ball joint plate comprising a conical surface.

13. The delivery system of claim 1, wherein the main knob assembly is in a normally closed configuration.

14. The delivery system of claim 1, wherein the tongue assembly comprises one or more tongues.

15. The delivery system of claim 1, wherein the multilumen cart comprises a bipod cover with a corresponding pattern with respect to a pattern of the stabilizing tool.

16. The delivery system of claim 1, wherein the multilumen cart comprises a sealing mechanism, a stabilizing tool handle, a stabilizing tool lock rail, and one or more multilumen cart rails.

17. The delivery system of claim 16, wherein the multilumen cart further comprises an actuation knob configured to open and lock the stabilizing tool handle to the multilumen cart.

18. The delivery system of claim 1, wherein the actuation mechanism of the back assembly comprises:
    a plurality of actuation knobs configured to move along one or more channels; and
    one or more springs configured to maintain tension to the sutures.

19. The delivery system of claim 1, wherein the suture routing mechanism of the back assembly comprises a suture cut configured to separate the sutures.

20. The delivery system of claim 1, wherein the tip lock mechanism is configured to connect to a flushing port to flush a tip lumen and to provide a passage to a guide wire.

* * * * *